United States Patent [19]
Motoyama

[11] 3,971,366
[45] July 27, 1976

[54] APPARATUS AND METHOD FOR MEASURING THE CONDITION OF THE MERIDIANS AND THE CORRESPONDING INTERNAL ORGANS OF THE LIVING BODY

[76] Inventor: Hiroshi Motoyama, 4-11-7, Inokashira, Mitaka, Tokyo, Japan

[22] Filed: Nov. 25, 1974

[21] Appl. No.: 527,150

[52] U.S. Cl. .......................... 128/2.1 Z; 128/2.1 E; 128/DIG. 4
[51] Int. Cl.² ......................................... A61B 5/04
[58] Field of Search ........... 128/2.1 R, 2.1 Z, 2.1 C, 128/2.1 B, 2.1 M, 2.1 E, 2.06 E, DIG. 4, 411, 417, 418

[56] References Cited
UNITED STATES PATENTS

| | | | |
|---|---|---|---|
| 2,308,933 | 1/1943 | Raesler | 128/2.1 R |
| 3,067,749 | 12/1962 | Walters | 128/418 |
| 3,195,533 | 7/1965 | Fischer | 128/2.1 B |
| 3,513,834 | 5/1970 | Suzuki et al. | 128/2.1 B |
| 3,598,112 | 8/1971 | Figar | 128/2.1 R |
| 3,641,993 | 2/1972 | Gaarder | 128/2.1 M |
| 3,834,374 | 9/1974 | Ensanian | 128/2.1 R |
| 3,841,309 | 10/1974 | Salter et al. | 128/2.1 B |

FOREIGN PATENTS OR APPLICATIONS

| | | | |
|---|---|---|---|
| 274,612 | 7/1951 | Switzerland | 128/DIG. 4 |

OTHER PUBLICATIONS
Takamura et al., "Highly Reliable Skin Electrodes," Toshiba Review, May–June 1970, pp. 11–16.

Primary Examiner—Robert W. Michell
Assistant Examiner—Lee S. Cohen
Attorney, Agent, or Firm—Wenderoth, Lind and Ponack

[57] ABSTRACT

An apparatus which diagnoses the functional condition of every internal organ and the balance condition of the autonomic nervous system in a living body has a reference electrode firmly attached to a part of the living body, a plurality of differential electrodes firmly attached to each of specific minute points which are located symmetrically in the tips of the members of a living body, a detection circuit to which the electrodes are connected to detect electric resistance in the surface layer of the living body generated between the reference electrode and the respective differential electrodes, an average value measurement circuit connected to the detecting circuit to obtain an average value from the detected output and a maximum value measurement circuit connected to the detection circuit to obtain a maximum value from said output. The apparatus diagnoses the function of every internal organ by measuring the change of electric resistance at a plurality of specific points in the surface layer of the living body which are directly related to the internal organ.

5 Claims, 18 Drawing Figures

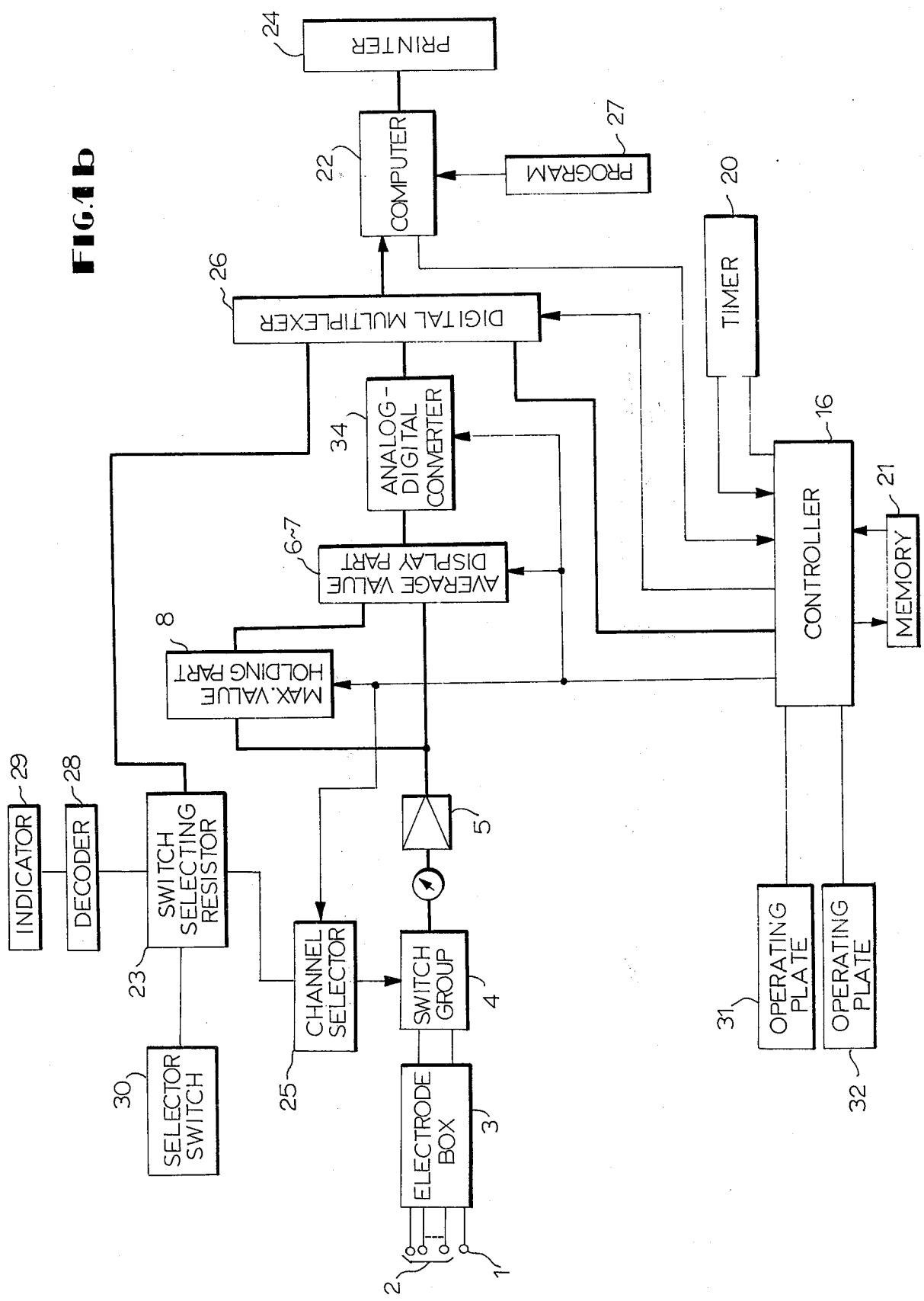

SUBJECT: ♀ 24.8.1972

$D\% = 4.06$  $\dfrac{Ri}{X_{LR}} = 1.68$  $D\% = 0.88$  $\dfrac{Li}{X_{LR}} = 1.47$  $\dfrac{Ri}{X_{LR}} = 1.01$ $\dfrac{L3}{X_{LR}} = 3.78$

LEFT LARGE-INTESTINE MERIDIAN — θ=62° — POLARIZATION

LEFT HEART-CONSTRICTOR MERIDIAN — θ=57°

RIGHT LARGE-INTESTINE MERIDIAN — θ=53° — POLARIZATION

LEFT DIAPHRAGM MERIDIAN — θ=46°

RIGHT HEART-CONSTRICTOR MERIDIAN — θ=54°

RIGHT DIAPHRAGM MERIDIAN — θ=64°

FIG.6

APPARATUS AND METHOD FOR MEASURING THE CONDITION OF THE MERIDIANS AND THE CORRESPONDING INTERNAL ORGANS OF THE LIVING BODY

BACKGROUND OF THE INVENTION

The present invention relates to an apparatus which diagnoses the functional condition of every internal organ and the balance condition of the autonomic nervous system in the living body.

Generally speaking, Western medicine mainly uses the method of bio-chemical clinical inspection for inspecting and diagnosing the function of respective internal organs and the diseases thereof, except for electrocardiograms and the like utilized for detecting the function of the heart. In many cases, however, said method necessitates a lot of money, time and labor and, moreover, pain on the part of the patients who undergo the inspection.

On the contrary, it has been well-known that Oriental medicine, especially those aspects known as acupuncture and moxa cautery medicine, performs medical treatment by the following method. It acknowledges through its clinical experiences that there exists in the whole living body the systems called "Keraku". The systems can be designated as the stimulation sensitivity systems or stimulation reaction systems. It also acknowledges that these systems have a close relationship with some of the internal organs and with autonomic nerves which control these organs. It detects abnormal conditions of each reaction point of these systems (this point is called the Keketsu or, popularly, the Tsubo) and from these conditions diagnoses the existence of disease in each internal organ which is related to the corresponding reaction point. Furthermore, it restores the internal organ to the normal condition by means of giving physical stimulation, such as needle insertion, heat etc. to the reaction point which is in the abnormal condition.

BRIEF REVIEW OF THE PRIOR ART

Among numerous reaction points, those points which exhibit an abnormal condition have thus far been discovered and confirmed by the sensitivity of the finger tips of the diagnostician and the conscious reactions of the subjects themselves. However, said method requires much skill and many years of experience on the part of the diagnostician. Thus, there have been devised types of apparatus which can perform electrical detection and diagnosis of the condition of the reaction points not by depending upon the experience and skill of the diagnostician but by taking advantage of the fact that electric resistance falls off greatly at the reaction points in the skin. An apparatus called a "Skin Ammeter" or "Neurometer" is one example of such an apparatus. In using this apparatus, an electrode is firmly attached to the skin surface of a part of the body and a roller electrode is placed against and moved around the skin surface of another part of the body such as, for instance, the main body, hands, feet etc. Electric resistance or impedance which is developed between said two electrodes is detected and the change in resistance or impedance at every checking point is observed to diagnose the functional condition of each internal organ and the existence of disease and, in some cases, to perform medical treatment. However, the use of a skin ammeter has many shortcomings as follows.

a. In inspecting the main body etc., it takes a lot of time since there are too many reaction points (for instance, about 30 points) with respect to one system which corresponds to one internal organ.

b. The reaction points are located at various distances from the skin surface and have various sizes, and sometimes this makes it difficult to discover a particular point among them.

c. On account of the comparatively high voltage, i.e. 9 – 27 V, being applied to the skin, the electrical reaction incurred everywhere on the body surface provokes an excitation reaction as the roller electrode is touched repeatedly to the body surface for inspection, and frequently it becomes impossible to obtain accurate measured values.

A heat sensitivity meter is another kind of apparatus used to detect abnormality at the reaction points. Taking advantage of the fact that there are terminals of all systems in the tips of the fingers and toes, this apparatus gives a constant heat stimulation continuously to these tips until the subject begins to feel the heat. Every degree of the heat being felt is designated with a numerical value and conspicuously abnormal systems are indicated by the difference of the values to show the degree of sensitivity to the heat. This apparatus is useful, indeed, in checking the change of heat sensitivity around so-called terminal points of the stimulating sensitivity system and inspecting heat sensory nerves. However, it sometimes happens that the heat used for the measurement stimulates the fingers so as to raise the temperature of them as a whole or to change the sensitivity of the measured part, making it difficult to obtain accurate numeral values. In addition, said method sometimes causes considerable pain to the subjects.

Apart from said problem, another problem is that there exists a polarization phenomenon. Namely, a stimulation such as voltage etc. given to the living body, including the human body, generates therein reverse voltage trying to prevent the stimulation voltage from flowing through the body.

FIG. 7 shows a known equivalent circuit in the skin of a living body. When a conventional resistance meter is used to measure resistance to applied electric current between the terminals of said equivalent circuit, a pattern such as that of FIG. 7 (b) is obtained by recording the time-progressive change of the measured voltage value, but a pattern such as that of FIG. 7 (c), which is obtainable from the living body, is not obtainable.

It should be understood that said pattern of FIG. 7 (c) is obtainable when a reverse voltage producing cell, more particularly, an electrolyte cell is inserted into the equivalent circuit. This means that, when the voltage etc. is applied to the living body, the reverse voltage is generated therein trying to prevent current flow in the circuit. In its broadest meaning, such a polarization phenomenon as this is one of the functions of the home-o-static system to try to keep the living body i.n a constant condition and also it may be regarded as a defensive function of the living body. It is considered that the reverse voltage is generated in this instance in an extremely short time, such as 5 – 30 microseconds, and thenceforth equalizes with the average value of the measured voltage.

However, a skin ammeter or a neurometer etc. of the type used thus far has a conventional meter, such as an ammeter, for measuring the resistance value or impedance of the living body and, since such a conventional meter as this can only check a change which takes place in 15 – 20 milliseconds at most, it cannot detect said polarization phenomenon accurately but can only measure the equalized voltage value after a certain time has passed.

Incidentally, the present inventor invented a diagnosing apparatus (Patent Application in Japan No. 59,776 filed 1971) which can examine electrically the abnormal conditions of the reaction points at the finger tips of the hands and feet in order to inspect the functional condition of every internal organ.

These reaction points in the skin represent so-called terminal points of the systems called in Japanese "keiraku" which exist in the whole living body. These points exist at the finger tips of the hands and feet as one or two specific minute points, of which there are 28 terminal points in all. These terminal points are called, in Japanese, the "Seiketsu", which means a well or well-hole. They are located in the skin at a position spaced about 3 mm from the finger nails of the hands and feet. As shown by black points in FIG. 4, it is acknowledged through clinical experience that these respective minute points have a close relationship with some of the corresponding internal organic meridians. Further, these terminal points are located symmetrically at the finger tips of the hands and feet, respectively.

The diagnosing apparatus comprises a reference electrode, a plurality of differential electrodes and a resistance measuring meter connected to those electrodes.

By using said device, the present inventor conducted the following experiment. Each differential electrode was firmly attached to one of the 28 terminal points of all stimulation sensitivity systems, and a reference electrode was firmly attached to another part of the body. Then 2 – 3 V of DC voltage was applied between the reference electrode and the differential electrodes in order to measure the skin resistance value at every terminal. The difference between the measured values of corresponding symmetrical points on the left and right sides of the body was figured out and the average value of all differences was calculated and then the value of the difference between the left and right terminals was divided by the average value, i.e. the percent of the difference between individual left and right terminals relative to the average difference for all terminals.

The result of said experiment shows that a terminal of a system which corresponds to an internal organ having a subjective symptoms in any degree apparently shows a high percentage, namely, not lower than 1.21% of the difference between the left and right terminals. Also, much of the data confirmed that the use of this apparatus gave no pain to the subjects at all and that the inspection was very effective.

Said diagnosing apparatus was devised so as to make it possible to attach stimulating electrodes to the parts of the living body where neither a reference electrode nor a differential were attached and the resistance values of terminals which were located near the electrically stimulated parts were measured. The differences of the measured values were calculated and utilized as one of the standard values for judgment.

However, the present inventor realized that these measured values could not be perfectly effective by themselves since the polarization phenomenon in the living body was not sufficiently taken into consideration in using this apparatus. Also, it was considered possible that a functional change might be provoked in the living body as the result of the high voltage, such as 22 V, being applied through the stimulating electrodes.

SUMMARY OF THE INVENTION

The present invention is a further improvement of the apparatus previously devised.

Accordingly, the object of the present invention is to provide such an apparatus with the following function. Namely in inspecting the function of the living body by attaching electrodes to it and measuring the resistance values, the apparatus of the present invention measures the value of electric current which flows momentarily before said polarization phenomenon is generated, together with the current value after polarization. As a result, the measurement precision of said apparatus is excellent and the probability of correct diagnosis by using the same is very great.

The basic configuration of the apparatus of the present invention consists of:

a detection part which detects, at the user's option, the resistance of the surface layer of a living body between a reference electrode firmly attached to a part of the living body and a plurality of differential electrodes firmly attached to specific minute positions which are located symmetrically at the tips of the fingers and toes of the living body, an average value measuring part which calculates the average value from the output of the detection part, and a maximum value measuring part which calculates the maximum value from the output of said detection part.

In using this apparatus, the differential electrodes are firmly attached in a stable manner to 14 terminals which exist as reaction points, according to acupuncture and moxa cautery medicine, in given positions in the tips of the fingers in the left and right hands and the toes of the feet and, at the same time, a reference electrode is attached to another part of the body. The skin resistance of each terminal is measured separately and, at that time, both of the values of the current which flows momentarily before polarization and the same after polarization are simultaneously measured. As a result of finding out the correct difference of the current values by conducting measurements in this way, the apparatus is quite effective and accurate in performing inspection of the functional condition of the internal organs and autonomic nerves.

BRIEF DESCRIPTION OF THE DRAWINGS

In the Figures:

FIGS. 1a and 1b are block diagrams of the whole configuration of the apparatus of the present invention;

FIG. 6 is a series of graphs of a part of the measured values obtained by the use of an embodiment of the apparatus of the present invention.

DETAILED DESCRIPTION OF THE INVENTION

Figure 3:
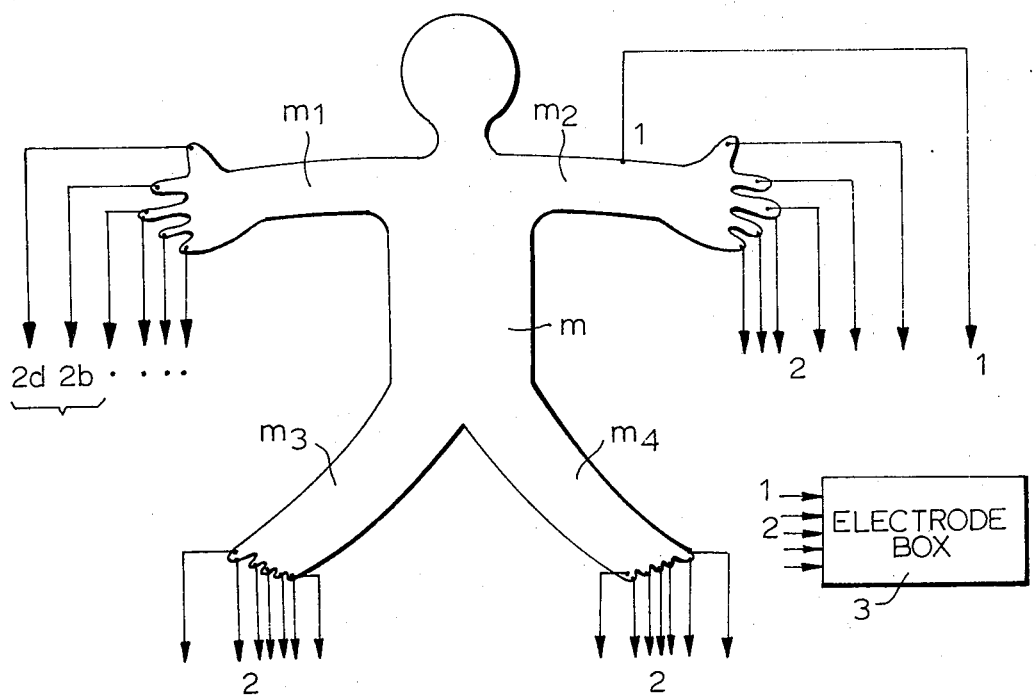
FIG. 3 is a diagram of terminals for attachment of the apparatus to a living body.
Figure 4:
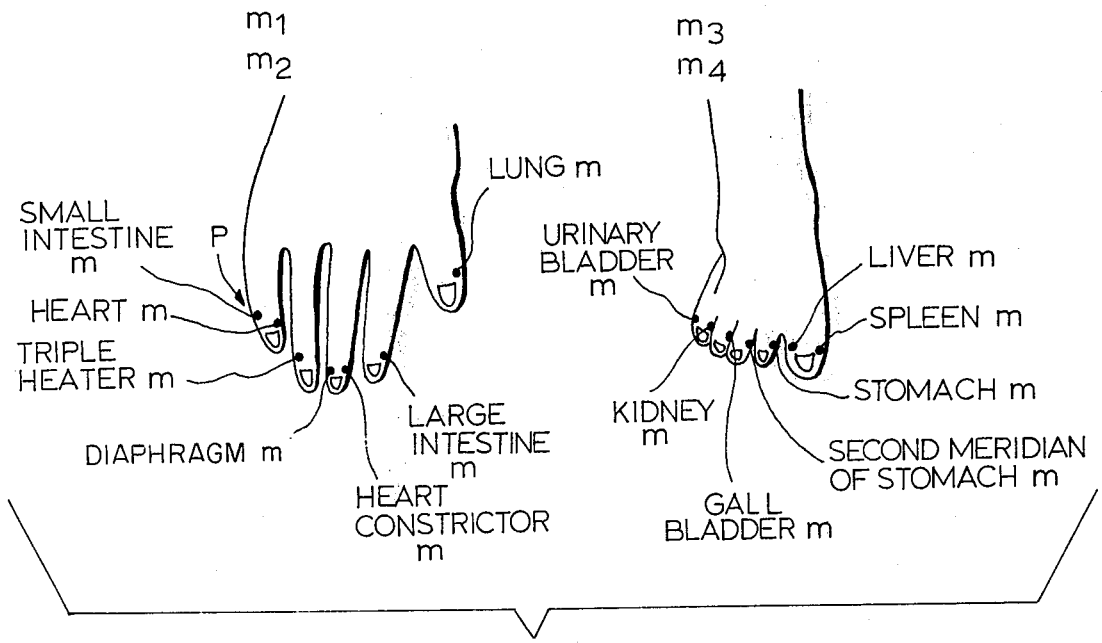
FIG. 4 is a diagram of the positions of terminals in the tips of the fingers and the toes of the human body.

A reference electrode 1 is provided which is to be firmly attached to an optional position on a living body m, such as shown in FIG. 3. A plurality of differential electrodes 2a, 2b . . . are provided which are to be firmly attached to the symmetrical tip parts of the living body m, for example, a given position on every finger tip of the both hands $m_1$, $m_2$ and the tips of the toes of both feet $m_3$, $m_4$ (see FIGS. 3 and 4).

Figure 5:
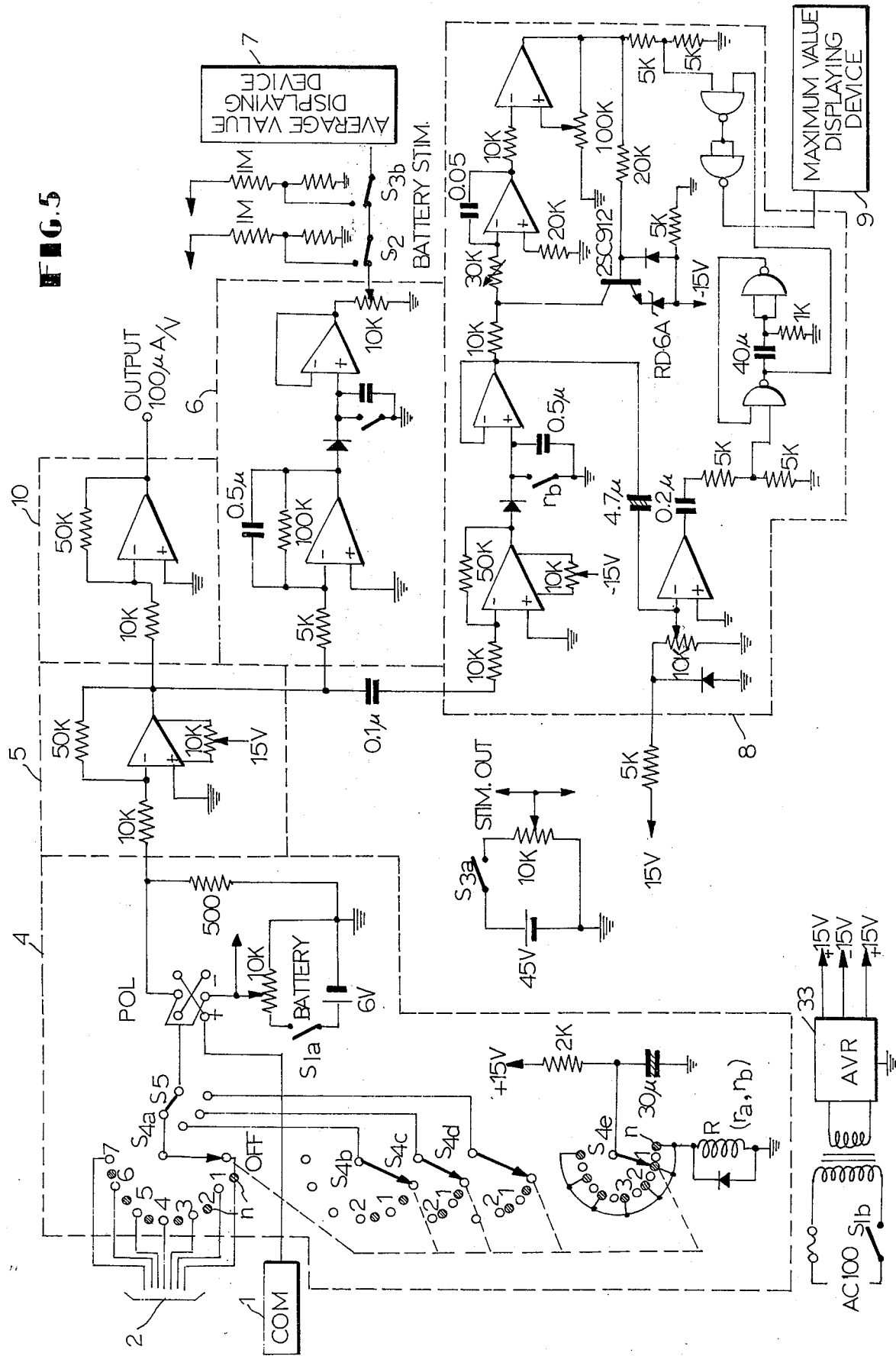
FIG. 5 is a circuit diagram of the apparatus according to the invention.
Figure 7A:
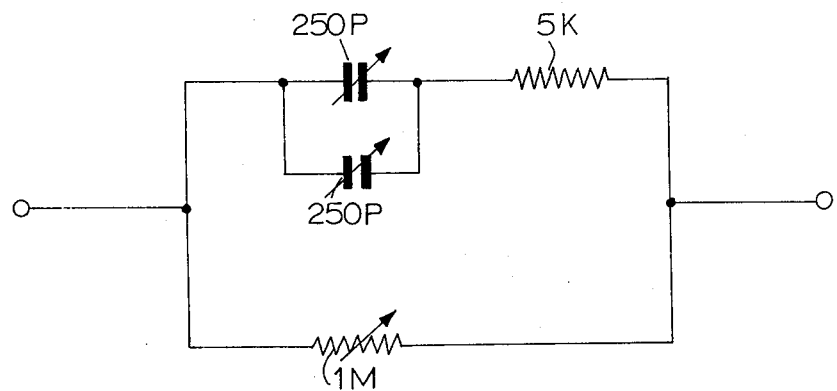
FIG. 7a is an equivalent circuit diagram.
Figure 7B:
FIGS. 7b, 7c and 8 are graphs of current values for explaining the theory of the present invention.
Figure 7C:

Reference numeral 3 designates an electrode box containing a detection circuit. The said electrodes 1 and 2a, 2b . . . are connected to the circuit in this electrode box, which in turn is connected to the remainder of the apparatus with a shielded cable having a shield effect. Reference numeral 4 designates a switch group which functions as an average value measurement part which is constructed as shown in the circuit diagram of FIG. 5, and it electrically detects the skin resistance, generally in terms of amperes, by supplying 2 ~ 3 V DC between each differential electrode 2a, 2b . . . and the reference electrode 1. In this case, each differential electrode can be switched into the circuit selectively under the control of a rotary switch $S_4$. This rotary switch $S_4$ comprises four interlocking rotary switches $S_{4a}$, $S_{4b}$, $S_{4c}$ and $S_{4d}$ in which there are provided with seven terminals respectively which are connected to a plurality of differential electrodes attached to the finger tips of the hands and feet. This rotary switch $S_4$ is constructed so that it can be changed over to respective differential electrodes attached to the tips of the fingers of the left and right hands and the toes of the left and right feet by means of the other switch $S_5$. Further, the rotary switch $S_{4e}$ is connected with the intermediate terminals (n) disposed between the respective seven terminals of the four interlocking rotary switches $S_{4a}$, $S_{4b}$, $S_{4c}$ and $S_{4d}$ above described. When the switch is changed over to the intermediate terminal, relays $r_a$ and $r_b$ are energized to reset a level value which is memorized in the integral circuit of an analogue holding part described below. Moreover, a switch POL is provided to reverse the polarity of voltage between said differential electrodes and said reference electrode.

Reference numeral 5 designates an amplifier which amplifies input current from said detection circuit 3 and switch group 4 and supplies the current values to an average value analogue holding part 6 and a maximum value analogue holding part 8, respectively. As shown in the circuit diagram of FIG. 5, this maximum value analogue holding part 8 comprises a plurality of amplifying circuits, "Nand" circuits and an integral circuit, and can detect and hold the peak voltage value of the input signal thereto. Average value analogue holding part 6 can hold the average level value of the signal detected by the detection circuit 3 after polarization. The holding parts 6 and 8 are connected to an average value displaying part 7 which displays a digital value and maximum value display part 9, respectively. Also, the amplifier 5 is connected with analogue storage etc. through output amplifier 10. Reference numeral 33 in FIG. 5 designates the power supply for the apparatus in said AMI.

As shown in FIG. 2 (a), each differential electrode has a hollow generally hemispherical part 11 about 9 mm in diameter made of an insulator such as synthetic resin or rubber and the like. There is a recess in the bottom of the hollow interior having a depth on the order of 1.1 mm and a depolarization electrode 12 about 4 mm in diameter constituted by a base of silver plated with silver chloride is fixed at the bottom of the recess. Said electrode 12 is connected with an external lead 13 and the remainder of the hollow interior is filled with conductive electrode paste 14 for example, a chloride. As shown in FIG. 2(b), the electrode paste is fixed by a rubber band 15 or the like to a terminal p in a tip of a finger or toe of a living body.

Figure 2A:
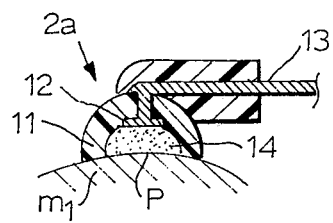
FIG. 2a is a sectional view of a differential electrode.
Figure 2B:
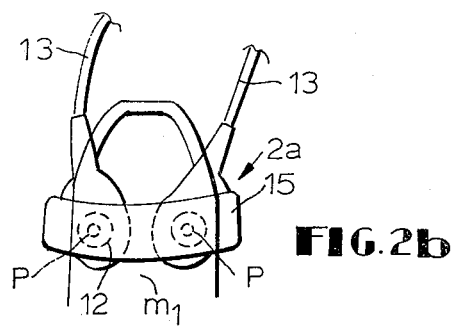
FIG. 2(b) is a front view of a differential electrode attached to the finger tip.
Figure 2C:
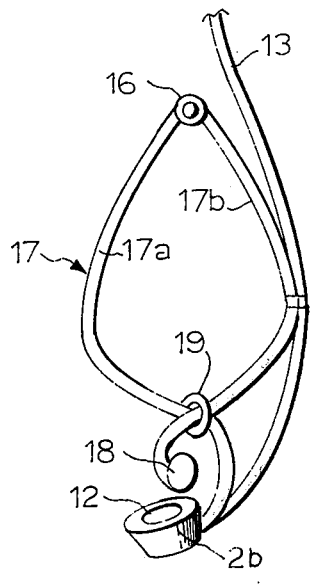
FIGS. 2(c) – 2(f) are front views of other embodiments of differential electrodes.

Alternatively, the differential electrodes can be provided at the end of a clip. FIG. 2(c) shows such clip with a differential electrode of FIG. 2a thereon. The differential electrode 2a is attached to the end part of one arm 17a of the clip and a supporting ball 18 is mounted on the end part of another arm 17b, the arms 17a and 17b being connected at a spring means 16 tending to move the arms toward each other. Ring 19 is hooked on the arms where they cross each other to prevent separation of the two arms. As shown in FIG. 2(d), the clip clamps a finger tip $m_1$ between the differential electrode 2a and the ball 18.

Figure 2E:
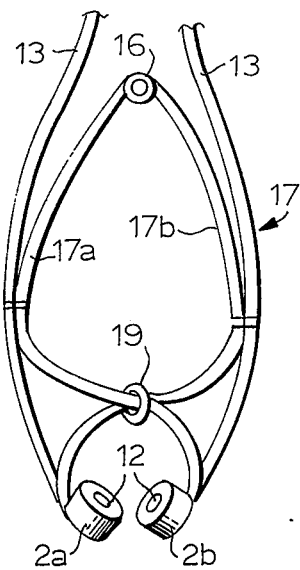

In an alternative embodiment shown in FIG. 2(e), differential electrodes 2a and 2b are provided at the end of each arm 17a and 17b or the clip. FIG. 2(f) shows the electrodes 2a and 2b clamped to two points on a finger tip $m_1$.

Figure 2G:
FIGS. 2(g) and 2(h) are plan views of reference electrodes.
Figure 2D:
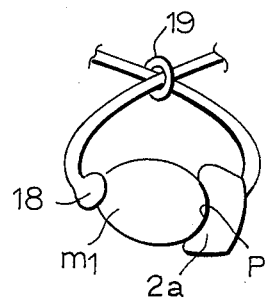
Figure 2H:
Figure 2F:
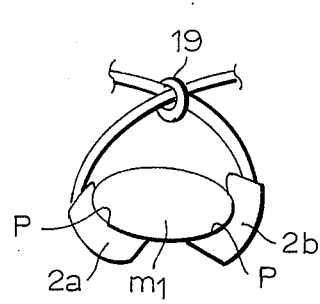

The reference electrode as shown in FIG. 2(g), can be a rectangular silver plate, which is 3 cm in length, 2 cm in width and about 0.3 mm thick, for example. Alternatively, four silver discs 2 cm in diameter as shown in FIG. 2h can be attached to the wrists of both hands and the ankles of both feet, respectively. The plate of FIG. 2g of the disc of FIG. 2h can be provided on a clip as shown in FIG. 2c.

Figure 1A:
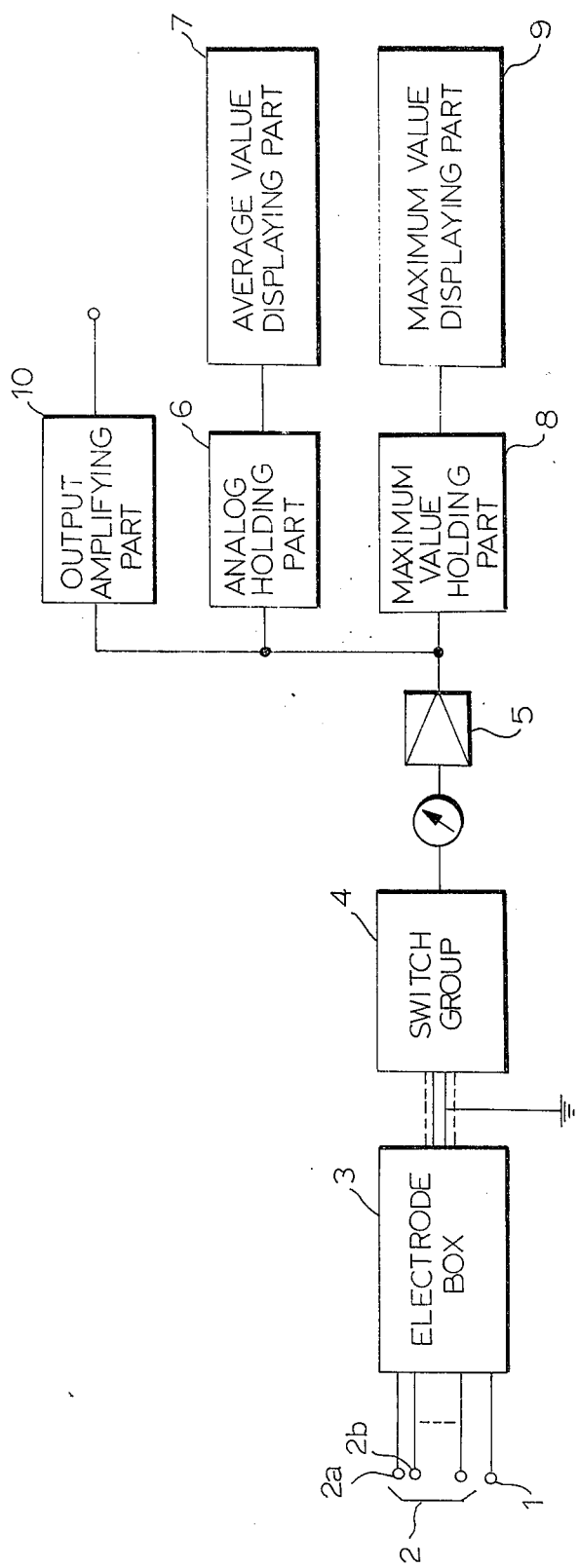

FIG. 1b shows a fully automatically controlled measuring apparatus which has a calculating circuit wherein measurement of the electric resistance and the necessary calculation are carried out, and the result of the calculation can be printed out according to a predetermined format.

The construction of said calculating circuit will be described in brief in the following. Reference numeral 16 designates a controller which changes over switch group 4 and then counts out the measured value at that time by controlling channel selector 25 through computer 22 and switch selecting resistor 23 according to the program memorized in memory 21, said value being printed out by printer 24 according to the predetermined format.

Furthermore, reference numeral 34 designates an analog-digital converter to convert the analog measurement into digital signals. Reference numeral 26 designates a digital multiplexer to process these digital signals. Numeral 27 designates a computing program input to the computer 22. Numeral 28 designates decoder to decode signals from an indicator 29 for controlling a switch selecting resistor. Further, numeral 30 is a selector switch for manually operating a switch group resistor. Reference numerals 31 and 32 designate operating plates to control the START and STOP etc. of the controlling part. Namely, the controller 16 changes over automatically among the various terminal points located in the skin by changing over switch group 4. Simultaneously with this operation, said controller can be used to reset the memorized values in the maximum value holding part 8 and the average value holding part 6 obtained by measuring the skin resistance at the terminal points, thereby starting preparation of the following measurement. In addition, this controller is constituted so as to supply the measured values to the computer 22 through the digital multiplexer 26 to control the performing of the desired calculation.

OPERATION OF THE APPARATUS

The operation of the apparatus of the present invention will now be described.

1. As shown in FIG. 3, the reference electrode is attached to an optional position on the body and, at the same time, differential electrodes $2a$, $2b$, . . . are attached to 14 terminal points on the left side of the body. As shown in FIG. 3, these terminal points are located symmetrically in the tips of the fingers of the left and right hands and the toes of the left and right feet and each terminal point has its own name related to each internal organ which has a relationship with one of 14 systems.

2. A voltage of 3 V DC is applied between the reference electrode and each of the differential electrodes and the DC resistance value (or current value) of the skin surface at each terminal point is measured separately for the left and right position by sequentially switching a lead contact. In each measurement, the resistance value before polarization and after polarization is measured as the maximum current value and the average current value, respectively.

3. Calculation

A. The polarization current value P relating to L (left) and R (right), respectively, is calculated by the following equation.

$$BP \text{ (Maximum Value)} - AP \text{ (Average Value)} = P$$

B. Each of the following items is calculated with respect to BP, AP and P.

(a). $|Di| = Li - Ri$ where $Li$, $Ri$ are the measured value at left and right terminals $i$.

b) $X_{LR} = \dfrac{\sum_{i=1}^{14} (Li + Ri)}{28}$ c) $\overline{D} = \dfrac{\sum_{i=1}^{14} |Di|}{14}$ d) $L \% = \dfrac{Ri}{X_{LR}}$ e) $R \% = \dfrac{Ri}{X_{LR}}$ f) $D \% = \dfrac{|Di|}{D}$ g) $\sigma (S, D)$ of $L \% - R \%$ $$= \sqrt{\dfrac{\sum_{i=1}^{28}(Li \sim Ri)^2}{N} - \left(\dfrac{\sum_{i=1}^{28}(Li \sim Ri)}{N}\right)^2}$$

Said calculation can be automatically conducted with said counting circuit simultaneously with the measurement of the electric resistance. The results of the calculation are shown in Tables 1 and 2. (The subject is male. The chief complaints and disease record is as shown in Table 3.) Then, the difference of the values between the left and right are compared with the subjective symptoms of the subject or with the results of a general examination of the subject.

From the results of said measurements, a judgment can be made as follows.

When the difference between the values at the left and right terminal points for a given system related to an internal organ is great, especially when the numerical value of the difference between the left and right terminals divided by the smaller value is not less than 1, it can be judged that the function of the internal organ is instable.

For example, the difference between the values for the left and right for the liver system, stomach system, kidney system, lung system, adrenal glands system etc. in Table 1 (all underlined) are judged abnormal.

As shown in Table 2, these judgments mostly coincide with the chief complaints reported by a subject in the present disease record, for example, as follows:

1. "I have loose bowels at times."
2. "I have been advised to take care of the liver since a group physical examination."
3. "I had undergone an operation for the lungs 10 years ago."

(Table 1)

| Foot Resistance value | 3V Left | Right | Terminal | Difference | % | Li/xLR | Ri/xLR |
|---|---|---|---|---|---|---|---|
| Before Polarization | 149 | 172 | Spleen Meridian | | | 1.06 | 1.22 |
| After polarization | 7.5 | 8.7 | | 1.2 | 0.2 | 0.75 | 0.87 |
| BP | 123 | 178 | Liver Meridian | | | 0.87 | 1.26 |
| AP | 19.4 | 10.3 | | 9.1 | 1.56 | 1.94 | 1.03 |
| BP | 137 | 126 | Stomach meridian | | | 0.94 | 0.89 |
| AP | 3.2 | 16.6 | | 12.6 | 2.16 | 0.32 | 1.66 |
| BP | 140 | 155 | | | | 0.99 | 1.1 |

(Table 1)-continued

| Foot Resistance value | 3V Left | Right | Terminal | Difference | % | Li/xLR | Ri/xLR |
|---|---|---|---|---|---|---|---|
| AP | 7.5 | 6.8 | Second meridian of stomach | 0.7 | 0.12 | 0.75 | 0.68 |
| BP | 141 | 165 | | | | 1.0 | 1.17 |
| AP | 8.6 | 5.1 | Gall-bladder meridian | 3.5 | 0.6 | 0.86 | 0.51 |
| BP | 129 | 153 | | | | 0.92 | 1.09 |
| AP | 6.4 | 24.6 | Kidney meridian | 18.2 | 3.12 | 0.64 | 2.46 |
| BP | 133 | 131 | | | | 0.94 | 0.93 |
| AP | 3.1 | 5.1 | Urinary-bladder meridian | 2 | 0.34 | 0.31 | 0.51 |

(Table 2)

| Hand Resistance Value | 3V Left | Right | Terminal | Difference | % | Li/xLR | Li/xLR |
|---|---|---|---|---|---|---|---|
| BP | 148 | 133 | | | | 1.05 | 0.94 |
| AP | 14.4 | 10.2 | Lung meridian | 4.2 | 0.72 | 1.44 | 1.02 |
| BP | 139 | 145 | | | | 0.99 | 1.03 |
| AP | 14.7 | 12.6 | Large intestine meridian | 2.1 | 0.36 | 1.47 | 1.26 |
| BP | 143 | 138 | | | | 1.01 | 0.98 |
| AP | 11.8 | 6.6 | Heart-Constriction meridian | 5.2 | 0.89 | 1.18 | 0.66 |
| BP | 120 | 144 | | | | 0.85 | 1.02 |
| AP | 6.2 | 9.2 | Diaphragm meridian | 3 | 0.51 | 0.62 | 0.92 |
| BP | 144 | 149 | | | | 1.02 | 1.06 |
| AP | 12.6 | 23.3 | Triple heater meridian | 10.7 | 1.83 | 1.26 | 2.33 |
| BP | 128 | 126 | | | | 0.91 | 0.89 |
| AP | 10.8 | 4.8 | Heart meridian | 6 | 1.02 | 1.08 | 0.48 |
| BP | 128 | 109 | | | | 0.91 | 0.77 |
| AP | 6.1 | 3.0 | Small intestine meridian | 3.1 | 0.53 | 0.61 | 0.3 |

(Table 3) Date of inspection: October 14, 1972. Past and present disease record and Chief complaints:
Have loose bowels at times.
Advised to take care of the liver.
Underwent operation for the lungs 10 years ago.

| | Terminal Measured value | Left & right hands Left & right feet | Difference (L-R) |
|---|---|---|---|
| Before polarization | $\Sigma X$ | 3926.0 | |
| | $\Sigma X^2$ | 556904.0 | |
| | $\bar{X}$ | 140.2142 | |
| | $\sigma$ | 15.1461 | |
| After polarization | $\Sigma X$ | 279.2 | 81.6 |
| | $\Sigma X^2$ | 3664.06 | 809.18 |
| | $\bar{X}$ | 9.9714 | 5.8285 |

-continued

| Terminal Measured value | Left & right hands Left & right feet | Difference (L-R) |
|---|---|---|
| $\sigma$ | 5.6062 | 4.8813 |

Note $\sigma_1$ is $\sigma$ of each measured value of 28 terminals.
$\sigma_2$ is $\sigma$ of each difference of values between the left and right of 14 systems.
% of difference is obtained by dividing difference $i$ by difference.
$\bar{x}$ of the difference values is the average value of 14 difference values.

FIG. 6 is a series of graphs of some of the measured values taken out analogically from the values measured at the terminal pionts of each system for another subject (female). In this graph, $L_2/xLR = 3.78$ for the left large intestine terminal is higher than the values of the other parts. Also, $\theta = 62°$, which is the angle at the extreme point of the curve after polarization with respect to the vertical direction, is comparatively great (about 50° or so for the other parts) and, accordingly, it can be judged that this internal organ is abnormal.

In connection with said embodiment, an explanation will be given regarding the electro-physiological meaning of the value of electric current generated by the polarization phenomenon in measuring the skin resistance of the living body.

Figure 8:
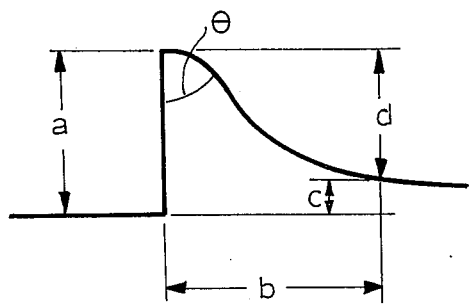

When a stimulation-like voltage is given to the skin of the living body, there is generally generated a waveform having the shape as shown in FIG. 8. In this figure, $a = $ the value before polarization, $b = $ the time of polarization (usually 2 m s), $c = $ the current value observable by an ammeter and $d = $ the amount of polarization.

Now, as the result of obtaining said waveforms, it becomes possible to set up various patterns which will indicate when the function of the organ is abnormal. When the value before polarization is small as in said example, electrically it means that the intrinsic skin resistance has become great. In this case, it can be physiologically considered that the cells of the surface skin etc. have degenerated and the resistance of cellular membrane is great; metabolization is lowered; the voltage inside and outside of the cells becomes stationary; the blood flow into this region decreases and so on.

Secondly, a low value of polarization indicates that the defensive function is lowered.

As the result, the current value after polarization is large in spite of the current value before polarization being small. This is a typical pattern of the case where the function of the concerned system and the corresponding internal organ is instable and abnormal.

The apparatus of the present invention can obtain the measured values separately in several stages ranging from the maximum value before polarization to the value after polarization by means of the analogue recording apparatus and this makes it possible to obtain various patterns of polarization shown in FIG. 6.

The pattern of polarization in FIG. 6 shows that the angle $\theta$ at the extreme point of the curve is not sharp but round. Also, the time of polarization is long and instable. Electrically speaking, the round angle $\theta$ at the extreme point is formed due to the leakage of the cell capacity. In other words, this indicates such condition as the cells have degenerated, their proper function as a condenser is lowered and their insulating capacity is worsened.

The result of checking and comparing the values measured before and after polarization sheds light on many things, which have not been clear so far, such as the condition of polarization, the condition of the defensive function of the living body, the condition of the cellular organ at the measuring points etc. and eventually makes the diagnosis more accurate.

ADVANTAGES OF THE INVENTION

As explained in connection with the embodiments described hereinabove, the present invention is an apparatus with the following configuration and function. In order to inspect the functional condition of the living body, the skin resistance values (or the current values) between the differential electrodes and the reference electrode are measured individually. In this instance, the differential electrodes are firmly attached with little effort to 14 terminal points of respective stimulation sensitivity systems which are located near the tips of the fingers of the left and right hands and the toes of the left and right feet. The reference electrode is firmly attached to another optional part of the living body. The functional condition of every internal organ and the existence of a disease thereof is diagnosed by making use of the difference of said resistance values at the left and right terminal points for the same system.

The use of this apparatus has the following excellent effect when compared with the methods of diagnosis used in the past and the use of apparatus so far devised for the same purposes as this apparatus.

1. The examination of the function of the internal organs in the past used to be conducted mostly by the biochemical method and it necessitated a lot of time, expense and labor. On the contrary, when the apparatus of the present invention is used, it is possible to grasp the functional condition of every internal organ in a very short time (20 minutes) and the labor and expense for the examination are relatively low.

2. In the clinical inspection in the past, it was often the case that a subject had to endure pain on account of being injected with liquid medicine or having a stomach-camera or some similar diagnostic instrument inserted into him, but the apparatus of the present invention causes no such pain.

3. The clinical inspection in the past could tell nothing further than the present functional condition or the condition of present illness. However, the use of the apparatus of the present invention makes the following things practicable: diagnosing the present functional condition of the autonomic nerves in the whole body; judging the reaction of the same at the time before and after polarization; telling the kind of the internal organs which show functional abnormality or instability; foreseeing illness which is subject may have in the future and so on. For example, if the reaction before and after a stimulation being given is a sympathetic nervous excitation type and it is observed that the autonomic nerves are mentally instable, it can be diagnosed that the subject can possibly be affected with high blood pressure, angina pectoris, etc.

4. The use of a skin ammeter involves many problems as follows:

a. It takes long time for examination.

b. It is difficult to find out the reaction points needed.

c. It is impossible to obtain accurate measured values on account of electrical reaction on the surface of the body, and so on.

On the other hand, the apparatus of the present invention makes it possible to diagnose accurately the abnormal condition of the systems related to every internal organ since the apparatus has the following advantages:

a. The operation of installing the differential electrodes is very simple and it does not take any significant time to prepare for examination since the measuring points are minute spots located in specific positions on the tips of the fingers and toes at the terminals of the systems which correspond with the internal organs, respectively, and in attaching the electrodes, rubber loops etc. can be used to make the operation smooth.

b. Using the electrode paste insures that the points corresponding to the terminals and the differential electrodes maintain uniform contact with each other and maintain a stabilized electrical connection, which in turn makes the measurement of the values accurate.

c. Since the voltage applied is as low as only 3 V and the electrodes are made of depolarizing material and, in addition, the measurement is performed in 1 to 2 seconds, there can be almost no chance that the electrical nature of the position where the measurement is made will be changed by the effect of the measuring voltage or current.

5. The prior art heat sensitivity meter has the following shortcomings:

a. The condition of the body at the position of the measurement is changed by heat stimulation and this makes it difficult to obtain accurate measured values at the time before and after the stimulation is given.

b. This method causes pain to the subjects. Contrary to this, in using the apparatus of the present invention, there is almost no change at the position of measurement since the voltage applied to the electrodes is very low and this makes it possible to measure accurately the change of the resistance values at the terminal points at a time before and after polarization, inclusive of the maximum values and the average values. In this way, it becomes practicable to grasp clearly the tendency of every internal organ and that of the autonomic nervous function in the whole body by examining the change of the resistance values at a time before and after polarization.

What is claimed is:

1. A visceral/automatic nervous function diagnosing apparatus comprising a reference electrode which is firmly attachable to a part of the living body, a plurality of differential electrodes firmly attachable to 14 pairs of specific minute points at the finger tips of the hands and feet of the living body, detecting circuit means to which said electrodes are connected for detecting electric resistance in the surface layer of the living body generated between said reference electrode and the respective differential electrodes and having a switching means for switching the connection between said reference electrode and respective differential electrodes, a maximum value measurement means connected to said detecting circuit means for obtaining a maximum value of the output of said detecting circuit means, an average value measurement means connected to said detection circuit means for obtaining an average value of the output of said detecting circuit means, and comparison and displaying means for comparing the maximum value and the average value and for displaying the results obtained from the comparison.

2. An apparatus as claimed in claim 1 further comprising a supporting clip for at least one of said differential electrodes, said clip having a pair of arms joined at one end and having spring means at said one end urging said arms toward each other, the other end of at least one arm having a differential electrode thereon.

3. An apparatus as claimed in claim 2 in which both arms have a differential electrode thereon.

4. An apparatus as claimed in claim 1 in which each differential electrode has a hollow generally curved part having the open side thereof shaped to be attachable to the side of a tip of an extremity of the living body, a depolarization electrode in the bottom of said hollow interior and electrode paste filling said hollow interior.

5. A method of diagnosing the condition of internal organs of the living body comprising the steps of firmly attaching a reference electrode to an optional point of the living body while firmly attaching differential electrodes to fourteen pairs of minute points at the finger tips of the hands and feet of the living body, detecting the electric resistance generated in the surface layer of the living body between the reference electrode and the respective differential electrodes by individually applying a d.c. voltage between said reference electrode and the respectively differential electrodes for determining the maximum value of the electric resistance, detecting the electric resistance reduced by polarization at the respective specific parts immediately after applying the d.c. voltage for determining said maximum electric resistance value for determining the average value of the electric resistance, and comparing the maximum value with the average value for the respective specific parts and indicating the results of such comparison.

* * * * *